United States Patent
Smith

(10) Patent No.: US 8,465,848 B2
(45) Date of Patent: Jun. 18, 2013

(54) BENZOFLUORENES FOR LUMINESCENT APPLICATIONS

(75) Inventor: Eric Maurice Smith, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 720 days.

(21) Appl. No.: 11/960,889

(22) Filed: Dec. 20, 2007

(65) Prior Publication Data

US 2008/0160348 A1    Jul. 3, 2008

Related U.S. Application Data

(60) Provisional application No. 60/877,772, filed on Dec. 29, 2006.

(51) Int. Cl.
*H01L 51/54* (2006.01)
*C07C 211/58* (2006.01)

(52) U.S. Cl.
USPC ........... 428/690; 428/917; 313/504; 313/506; 564/306

(58) Field of Classification Search
None
See application file for complete search history.

(56) References Cited

U.S. PATENT DOCUMENTS

| | | | |
|---|---|---|---|
| 3,849,458 A | 11/1974 | Dinh | |
| 5,247,190 A | 9/1993 | Friend et al. | |
| 5,408,109 A | 4/1995 | Heeger et al. | |
| 5,707,747 A | 1/1998 | Tomiyama et al. | |
| 5,929,194 A | 7/1999 | Woo et al. | |
| 5,962,631 A | 10/1999 | Woo et al. | |
| 6,259,202 B1 | 7/2001 | Sturm et al. | |
| 6,579,630 B2 | 6/2003 | Li et al. | |
| 6,686,065 B2 * | 2/2004 | Chen | 428/690 |
| 6,849,348 B2 * | 2/2005 | Zheng et al. | 428/690 |
| 6,872,475 B2 | 3/2005 | Chen et al. | |
| 6,953,705 B2 | 10/2005 | Prakash | |
| 7,023,013 B2 | 4/2006 | Ricks et al. | |
| 7,189,989 B2 | 3/2007 | Ise | |
| 7,235,420 B2 | 6/2007 | Prakash et al. | |
| 7,425,653 B2 * | 9/2008 | Funahashi | 564/434 |
| 7,540,978 B2 | 6/2009 | Pfeiffer et al. | |
| 7,887,933 B2 | 2/2011 | Kathirgamanathan et al. | |
| 8,063,399 B2 | 11/2011 | Johansson et al. | |
| 2001/0026878 A1 | 10/2001 | Woo et al. | |
| 2002/0155319 A1 | 10/2002 | Kawamura et al. | |
| 2003/0118866 A1 * | 6/2003 | Oh et al. | 428/690 |
| 2003/0134140 A1 | 7/2003 | Li | |
| 2003/0143422 A1 * | 7/2003 | Chen | 428/690 |
| 2004/0004433 A1 | 1/2004 | Lamansky et al. | |
| 2004/0038459 A1 | 2/2004 | Brown et al. | |

(Continued)

FOREIGN PATENT DOCUMENTS

| EP | 443 861 B1 | 7/1995 |
|---|---|---|
| EP | 1277824 A1 | 1/2003 |

(Continued)

OTHER PUBLICATIONS

Bolton et al., J. of Chem. Research Synopses, 1977, (5), p. 149.*

(Continued)

*Primary Examiner* — Dawn Garrett

(57) ABSTRACT

This invention relates to electroluminescent benzofluorenes that are useful in electroluminescent applications. It also relates to electronic devices in which the active layer includes such a benzofluorene composition.

12 Claims, 1 Drawing Sheet

Schematic of a light-emitting device

U.S. PATENT DOCUMENTS

| | | | |
|---|---|---|---|
| 2004/0076853 A1* | 4/2004 | Jarikov | 428/690 |
| 2004/0082250 A1 | 4/2004 | Haoto | |
| 2004/0102577 A1 | 5/2004 | Hsu et al. | |
| 2004/0127637 A1 | 7/2004 | Hsu et al. | |
| 2004/0131880 A1* | 7/2004 | Zheng et al. | 428/690 |
| 2004/0263067 A1 | 12/2004 | Saitoh et al. | |
| 2005/0064233 A1 | 3/2005 | Matsuura et al. | |
| 2005/0073249 A1 | 4/2005 | Morii et al. | |
| 2005/0184287 A1 | 8/2005 | Herron et al. | |
| 2005/0186106 A1 | 8/2005 | Li et al. | |
| 2005/0191776 A1 | 9/2005 | Lamansky et al. | |
| 2005/0205860 A1 | 9/2005 | Hsu et al. | |
| 2006/0033421 A1 | 2/2006 | Matsuura et al. | |
| 2006/0152146 A1* | 7/2006 | Funahashi | 313/504 |
| 2006/0216411 A1 | 9/2006 | Steudel et al. | |
| 2007/0031588 A1 | 2/2007 | Nakayama | |
| 2007/0032632 A1 | 2/2007 | Tsukioka et al. | |
| 2007/0079927 A1 | 4/2007 | Lamansky et al. | |
| 2007/0096082 A1 | 5/2007 | Gaynor et al. | |
| 2007/0120466 A1* | 5/2007 | Arakane et al. | 313/504 |
| 2007/0181874 A1 | 8/2007 | Prakash et al. | |
| 2007/0228364 A1 | 10/2007 | Radu et al. | |
| 2008/0067924 A1 | 3/2008 | Prakash et al. | |
| 2008/0071049 A1 | 3/2008 | Radu et al. | |
| 2008/0097076 A1 | 4/2008 | Radu et al. | |
| 2008/0102312 A1 | 5/2008 | Parham et al. | |
| 2008/0138655 A1 | 6/2008 | Lecloux et al. | |
| 2008/0160347 A1* | 7/2008 | Wang et al. | 428/704 |
| 2008/0233429 A1* | 9/2008 | Oguma et al. | 428/690 |
| 2009/0051281 A1 | 2/2009 | Inoue | |
| 2009/0184312 A1* | 7/2009 | Nishiyama et al. | 257/40 |
| 2009/0184635 A1 | 7/2009 | Pan et al. | |
| 2009/0206748 A1 | 8/2009 | Moriwaki et al. | |
| 2010/0108989 A1 | 5/2010 | Büsing et al. | |
| 2010/0187506 A1 | 7/2010 | Park et al. | |
| 2011/0095269 A1 | 4/2011 | Zhang et al. | |

FOREIGN PATENT DOCUMENTS

| | | |
|---|---|---|
| EP | 1624500 A1 | 2/2006 |
| EP | 1933603 A1 | 6/2008 |
| JP | 08167479 A | 6/1996 |
| JP | 11224779 A | 8/1999 |
| JP | 11338172 A | 12/1999 |
| JP | 2000068073 A | 3/2000 |
| JP | 2000186066 A | 7/2000 |
| JP | 2001039933 A | 2/2001 |
| JP | 2001226331 A | 8/2001 |
| JP | 2002506481 A | 2/2002 |
| JP | 2002293888 A | 10/2002 |
| JP | 2003026641 A | 1/2003 |
| JP | 2003238501 A | 8/2003 |
| JP | 2004014187 A | 1/2004 |
| JP | 2004107292 A | 4/2004 |
| JP | 2006328037 A | 12/2006 |
| JP | 2007182432 A | 7/2007 |
| KR | 1020050073233 A | 7/2005 |
| KR | 100702763 B1 | 4/2007 |
| KR | 1020070091293 A | 9/2007 |
| KR | 100765728 B1 | 10/2007 |
| WO | 9954385 A1 | 10/1999 |
| WO | 0053565 A1 | 9/2000 |
| WO | 2004041901 A1 | 5/2004 |
| WO | 2005049546 A1 | 6/2005 |
| WO | 2005049548 A1 | 6/2005 |
| WO | 2005049689 A2 | 6/2005 |
| WO | 2005052027 A1 | 6/2005 |
| WO | 2006063852 A1 | 6/2006 |
| WO | 2006121237 A1 | 11/2006 |
| WO | 2007076146 A2 | 7/2007 |
| WO | 2007108666 A1 | 9/2007 |
| WO | 2008011953 A1 | 1/2008 |
| WO | 2008150828 A2 | 12/2008 |
| WO | 2008150940 A1 | 12/2008 |
| WO | 2008150942 A1 | 12/2008 |
| WO | 2009028902 A2 | 3/2009 |
| WO | 2009067419 A1 | 5/2009 |
| WO | 2009075223 A1 | 6/2009 |

OTHER PUBLICATIONS

CRC Handbook of Chemistry and Physics, 81st Edition, 2000.
John Markus, Photoconductive Cell, Electronics and Nucleonics Dictionary, 1966, pp. 470 & 476.
Y. Wang, Photoconductive Polymers, Kirk-Othmer Encyclopedia of Chemical Technology, 4th Edition, 1996, vol. 18:837-860.
Gustafsson et al., Flexible Light-Emitting Diodes Made From Soluble Conducting Polymers, Nature, 1992, vol. 357:477-479.
Boix et al., "Efficient H-D Exchange of Aromatic Compounds in Near-Critical D2O Catalysed by a Polymer-Supported Sulphonic Acid," Tetrahedron Letters 40, 1999, pp. 4433-4436.
Borello et al., "Photodetectors," Kirk-Othmer Encyclopedia of Chemical Technology, Fourth Edition, 1999, vol. 18, pp. 1537-1538.
Chen et al., "Efficient, Blue Light-Emitting Diodes Using Cross-Linked Layers of Polymeric Arylamine and Fluorene," Synthetic Metals, 1999, vol. 107, pp. 129-135.
Colon et al., "High Molecular Weight Aromatic Polymers by Nickel Coupling of Aryl Polychlorides," Journal of Polymer Science, Part A, Polymer Chemistry Edition, 1990, vol. 28, pp. 367-382.
Eaton et al., "Dihedral Angle of Biphenyl in Solution and the Molecular Force Field," Journal of the Chemical Society: Faraday Transactions 2, 1973, vol. 60, pp. 1601-1608.
Esaki et al., "Efficient H/D Exchange Reactions of Alkyl-Substituted Benzene Derivatives by Means of the Pd/C—H2—D2O System," Chemistry: A European Journal, 2007, vol. 13, pp. 4052-4063.
Guo et al., "Aromatic H/D Exchange Reaction Catalyzed by Groups 5 and 6 Metal Chlorides," Chinese Journal of Chemistry, 2005, vol. 23, pp. 341-344.
He et al., "A Hole-transporting material with Contollable Morphology Containing Binaphthyl and Triphenylamine Chromophores," Advanced Functional Materials, 2006, vol. 16, No. 10, pp. 1343-1348.
He et al., "High-efficiency Organic Polymer Light-emitting Heterostructure Devices on Flexible Plastic Substrates," Applied Physics Letters, 2000, vol. 76, No. 6, pp. 661-663.
Lee et al., "A Thermally Stable Hole Injection Material for Use in Organic Light-Emitting Diodes," Thin Solid Films, 2007, vol. 515, pp. 7726-7731.
Noji et al., "A New Catalytic System for Aerobic Oxidative Coupling of 2-Naphthol Derivatives by the Use of CuCl-Amine Complex: A Practical Synthesis of Binaphthol Derivatives," Tetrahedron Letters, 1994, vol. 35, No. 43, pp. 7983-7984.
Sajiki et al., "Efficient C—H/C—D Exchange Reaction on the Alkyl Side Chain of Aromatic Compounds Using Heterogeneous Pd/C in D2O," Org. Lett., 2004, vol. 6(9), pp. 1485-1487.
Watts et al., "A novel deuterium effect on dual charge-transfer and ligand-field emission of the cis-dichlorobis(2,2'-bipyridine)iridium(III) ion," Journal of the American Chemical Society, 1979, vol. 101(10), pp. 2742-2743.
Yamamoto et al., "Electrically conducting and thermally stable pi-conjugated poly(arylene)s prepared by organometallic process," Progress in Polymer Science, 1992, vol. 17, pp. 1153-1205.
Zhao et al., "Solid-State Dye-Sensitized Photovoltaic Device with Newly Designed Small Organic Molecule as Hole—Conductor," Chemical Physical Letters, 2007, vol. 445, pp. 259-264.
Zhu et al., "Effect of ITO Carrier Concentration on the Performance of Light-Emitting Diodes," 2000; Material Research Society; Chem Abstract 134: 122994.
PCT International Search Report for Application No. PCT/US2010/058865, counterpart to U.S. Appl. No. 12/643,257; Kim Jong Ho, Authorized Officer; KIPO; Oct. 21, 2011.
PCT International Search Report for Application No. PCT/US2007/018530, counterpart to U.S. Appl. No. 11/843,029; C. Meiners, Authorized Officer; Feb. 7, 2008.
PCT International Search Report for Application No. PCT/US2007/018531, counterpart to U.S. Appl. No. 11/843,041; D. Marsitzky, Authorized Officer; Feb. 26, 2008.

* cited by examiner

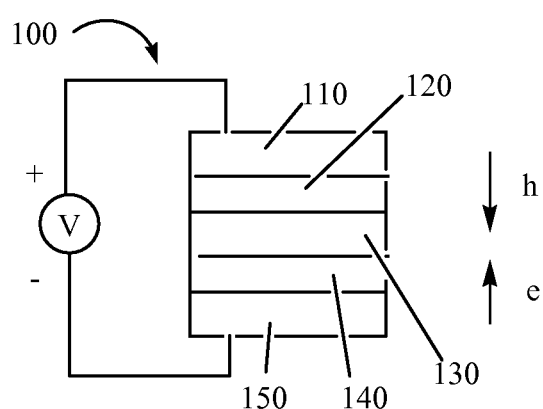
Schematic of a light-emitting device

BENZOFLUORENES FOR LUMINESCENT APPLICATIONS

RELATED APPLICATION DATA

This application claims priority under 35 U.S.C. §119(e) from U.S. Provisional Application No. 60/877,772 filed Dec. 29, 2006 which is incorporated by reference herein in its entirety.

BACKGROUND

1. Field of the Disclosure

This invention relates to electroluminescent benzofluorenes. It also relates to electronic devices in which the active layer includes such a benzofluorene composition.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, U.S. Pat. Nos. 5,247,190, 5,408,109, and Published European Patent Application 443 861.

However, there is a continuing need for electroluminescent compounds, especially compounds that are blue-emitting.

SUMMARY

There is provided a composition having Formula I:

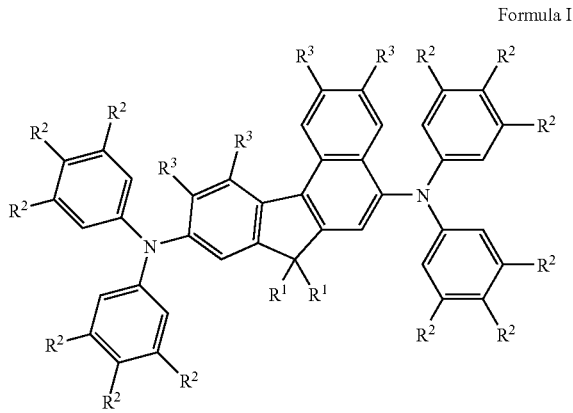

Formula I wherein each R is independently selected from the group consisting of hydrogen, halogen, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl.

There is also provided an electronic device comprising an active layer comprising the compound of Formula I.

BRIEF DESCRIPTION OF THE DRAWINGS

FIG. 1 is a schematic diagram of a light-emitting device (LED).

DEFINITION OF TERMS

As used herein, the term "compound" is intended to mean an electrically uncharged substance made up of molecules that further consist of atoms, wherein the atoms cannot be separated by physical means. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond). The term "photoactive" refers to any material that exhibits electroluminescence and/or photosensitivity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The IUPAC numbering system is used throughout, where the groups from the Periodic Table are numbered from left to right as 1-18 (CRC Handbook of Chemistry and Physics, 81$^{st}$ Edition, 2000).

DETAILED DESCRIPTION

One aspect of the present invention is a composition of Formula I:

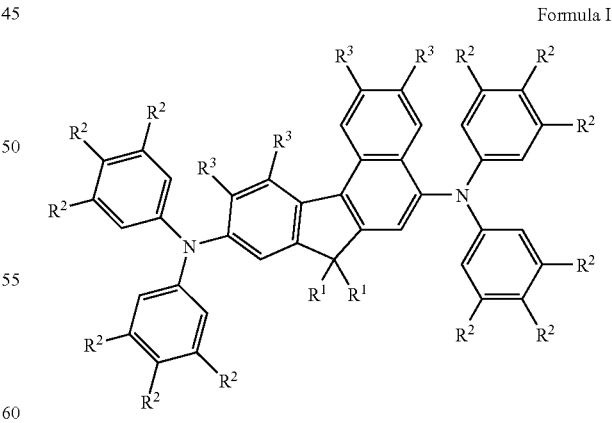

Formula I wherein each R is independently selected from the group consisting of hydrogen, halogen, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphory.

Suitable alkyl groups include $C_1$-$C_{20}$ substituted and unsubstituted alkyls. Suitable fluoroalkyls include $C_1$-$C_{20}$ alkyls in which one or more hydrogens have been replaced with fluorine. Fluoroalkyls include partially and fully fluorinated groups. Suitable aryls include substituted and unsubstituted phenyl and naphthyl groups. Suitable heteroaryls include substituted and unsubstituted pyridines, quinolines, isoquinolines, pyrimidines, pyrazines, pyridazines, purines, indoles, isoindoles, benzothiophenes, quinazolines, cinnolines, benzofurans, benzimidazoles, quinoxalines and indolines. Suitable diarylaminos, diarylphosphinos, and diarylphosphoryls include amino, phosphino, and phosphoryl groups, respectively, comprising two substituted or unsubstituted phenyl groups. Suitable dialkylaminos, dialkylphosphinos, and dialkylphosphoryls include amino, phosphino, and phosphoryl groups, respectively, comprising two substituted or unsubstituted $C_1$-$C_{10}$ alkyl groups. Suitable aryl(alkyl) amino groups include amino groups comprising one substituted or unsubstituted phenyl group and one substituted or unsubstituted $C_1$-$C_{10}$ alkyl group. Suitable arylthio (or arylseleno) groups include thio (or seleno) groups comprising one substituted or unsubstituted phenyl group. Suitable alkylthio (or alkylseleno) groups include thio (or seleno) groups comprising one $C_1$-$C_{10}$ substituted or unsubstituted alkyl group. Suitable aryloxy groups include oxy groups comprising one substituted or unsubstituted phenyl group. Suitable alkoxy groups include oxy groups comprising a substituted or unsubstituted $C_1$-$C_{10}$ alkyl group.

Suitable substituents for the aryl groups include halo, amino, silyl, and $C_1$-$C_{10}$ alkyl groups. Suitable substituents for the alkyl groups include amino, halo and silyl groups.

In some embodiments, both $R^1$ groups are alkyl groups. In some embodiments, the alkyl groups have from 1-10 carbon atoms.

In some embodiments, both $R^1$ groups are alkyl groups and all $R^2$ and $R^3$ groups are hydrogen.

In some embodiments, at least one $R^2$ is selected from the group consisting of fluoro, alkyl, and fluoroalkyl.

In some embodiments, both $R^1$ groups are alkyl groups, at least one $R^2$ is selected from the group consisting of fluoro, alkyl, and fluoroalkyl, and all $R^3$ groups are hydrogen.

The benzofluorene compounds described herein are neutral and non-ionic, and can be sublimed intact. Thin films of these materials obtained via vacuum deposition exhibit good to excellent electroluminescent properties and blue emission. Electronic Device A generic organic light emitting diode (OLED) consists of several thin-film layers: (1) a transparent anode, usually indium tin oxide (ITO) on glass, (2) a hole transport material, (3) a luminescent material, (4) an electron transport material, and (5) a metallic cathode (e.g. Al, Al/LiF, or a low work-function metal alloy). The electrons and holes are injected from the cathode and anode into the device, and are then induced to recombine within the luminescent layer by the use of hole-transport and electron-transport layers. Recombination of electrons and holes generates an excited state of the molecular species that emits light.

A typical OLED device structure is shown in FIG. 1. The device 100 has an anode layer 110 and a cathode layer 150. Adjacent to the anode is a layer 120 comprising hole transport material. Adjacent to the cathode is a layer 140 comprising an electron transport/anti-quenching material. Between the hole transport layer and the electron transport/anti-quenching layer is the photoactive layer 130. As an option, devices frequently have a hole injection layer 115 (not shown) between the anode and the hole transport layer, and may have another electron transport layer 145 (not shown), between the cathode the first electron transport layer. Layers 115, 120, 130, 140, and 145 are individually and collectively referred to as the active layers.

Depending upon the application of the device 100, the photoactive layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary,* 470 and 476 (McGraw-Hill, Inc. 1966).

Triarylmethane derivatives are particularly useful as the hole transport layer 120, and as a charge conducting host in the photoactive layer, 130. Examples of hole transport materials for layer 120 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)polysilane, and polyaniline. It is also possible to obtain hole transporting polymers by doping hole transporting molecules such as those mentioned above into polymers such as polystyrene and polycarbonate.

The other layers in the device can be made of any materials that are known to be useful in such layers.

The anode 110, is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 110 can also comprise an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

Examples of the photoactive layer 130 include all known electroluminescent materials. These electroluminescent complexes can be used alone, or doped into charge-carrying hosts, as noted above. The benzofluorenes of Formula I, in addition to being useful as emissive dopants in the photoactive layer, can also act as charge carrying hosts for other emissive dopants in the photoactive layer 130.

Examples of additional electron transport materials which can be used in layer 140 include metal chelated oxinoid compounds, such as tris(8-hydroxyquinolato)aluminum (Alq$_3$); bis(2-methyl-8-quinolinolato)(para-phenyl-phenolato)aluminum(III) (BAIQ); and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthroline derivatives such as 9,10-diphenylphenanthroline (DPA) and 2,9-dimethyl-4,7-diphenyl-1,10-phenanthroline (DDPA); and mixtures thereof. Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds, LiF, and Li$_2$O can also be deposited between the organic layer and the cathode layer to lower the operating voltage.

It is known to have other layers in organic electronic devices. For example, there can be a layer (not shown) between the anode 110 and hole transport layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, the hole transport layer 120, the electron transport layers 140 and 160, or cathode layer 150, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like. In general, the different layers will have the following range of thicknesses: anode 110, 500-5000 Å, preferably 1000-2000 Å; hole transport layer 120, 50-2000 Å, preferably 200-1000 Å; photoactive layer 130, 10-2000 Å, preferably 100-1000 Å; electron transport layers 140 and 160, 50-2000 Å, preferably 100-1000 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses will depend on the exact nature of the materials used.

The present invention also relates to an electronic device comprising at least one photoactive layer positioned between two electrical contact layers, wherein the at least one layer of the device includes the benzofluorene of Formula 1. Devices frequently have additional hole transport and electron transport layers.

The benzofluorene compounds described herein are particularly useful as the photoactive material in layer 130, or as electron transport material in layer 140. Preferably the benzofluorene compounds are used as the light-emitting material in diodes. Additional materials can be present in the emitting layer with the benzofluorene. For example, a fluorescent dye can be present to alter the color of emission. A diluent can also be added and such diluent can be a charge transport material or an inert matrix. A diluent can comprise polymeric materials, small molecule or mixtures thereof. A diluent can act as a processing aid, can improve the physical or electrical properties of films containing the benzofluorene. Non-limiting examples of suitable polymeric materials include poly(N-vinyl carbazole), polyfluorene, and polysilane. Non-limiting examples of suitable small molecules include 4,4'-N,N'-dicarbazole biphenyl, bis(2-methyl-8-quinolinolato)(para-phenylphenolato)aluminum(III) (BAIQ); and tertiary aromatic amines. When a diluent is used, the benzofluorene is generally present in a small amount. In one embodiment, the benzofluorene of Formula I is less than 20% by weight, based on the total weight of the layer. In another embodiment, the benzofluorene of Formula I is less than 10% by weight, based on the total weight of the layer.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials are also important considerations in selecting the electron and hole transport materials.

It is understood that the efficiency of devices made with the benzofluorenes described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

The benzofluorenes described herein often are phosphorescent and photoluminescent and can be useful in applications other than OLEDs, such as oxygen sensitive indicators and as phosphorescent indicators in bioassays.

Note that not all of the activities described above in the general description or the examples are required, that a portion of a specific activity may not be required, and that one or more further activities may be performed in addition to those described. Still further, the order in which activities are listed is not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

In some embodiments, the invention herein can be construed as excluding any element or process step that does not materially affect the basic and novel characteristics of the composition or process. Additionally, in some embodiments, the invention can be construed as excluding any element or process step not specified herein.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A composition compound of Formula I:

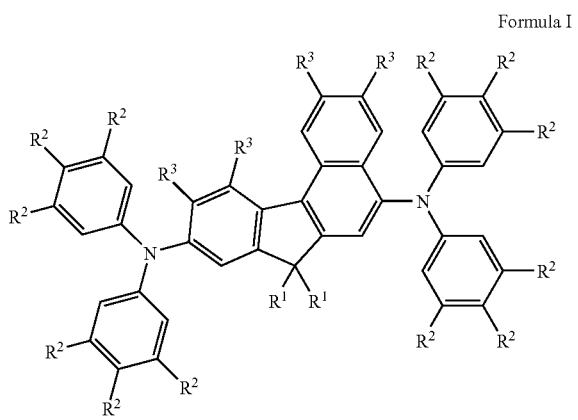

Formula I wherein each of $R^1$, $R^2$, and $R^3$ is independently selected from the group consisting of hydrogen, halogen, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl.

2. The composition compound of claim 1, wherein $R^1$ is the same or different at each occurrence and is an alkyl group, and $R^2$ and $R^3$ are hydrogen.

3. The composition compound of claim 1, wherein $R^1$ is the same or different at each occurrence and is an alkyl group, at least one $R^2$ is selected from the group consisting of fluoro, alkyl, and fluoroalkyl, and $R^3$ is hydrogen.

4. An organic electronic device comprising: a. a first electrical contact layer;
   b. a layer comprising a composition compound of Formula I:

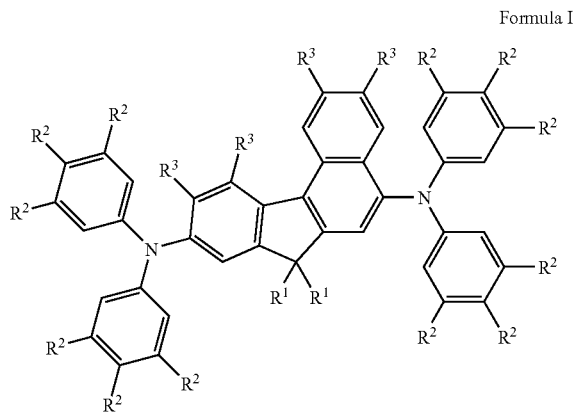

Formula I wherein each of $R^1$, $R^2$, and $R^3$ is independently selected from the group consisting of hydrogen, halogen, alkyl, fluoroalkyl, aryl, heteroaryl, diarylamino, dialkylamino, aryl(alkyl)amino, arylthio, alkylthio, arylseleno, alkylseleno, aryloxy, alkoxy, dialkylphosphino, diarylphosphino, dialkylphosphoryl, diarylphosphoryl, and thiophosphoryl; and
   c. a second electrical contact layer.

5. The device of claim 4, wherein $R^1$ is the same or different at each occurrence and is an alkyl group, and $R^2$ and $R^3$ are hydrogen.

6. The device of claim 4, wherein $R^1$ is the same or different at each occurrence and is an alkyl group, at least one $R^2$ is selected from the group consisting of fluoro, alkyl, and fluoroalkyl, and $R^3$ is hydrogen.

7. The device of claim 4, wherein the layer comprising a composition compound of Formula I is an active layer.

8. The device of claim 7, wherein the active layer is a photoactive layer.

9. The device of claim 8, wherein the compound is a dopant.

10. The device of claim 8, wherein the compound is a host.

11. The compound of claim 1 which, when formed into a film by vacuum deposition, is capable of emitting blue light.

12. The device of claim 4 wherein the layer comprising the compound of Formula I is capable of emitting blue light.

* * * * *